(12) United States Patent
Geissler et al.

(10) Patent No.: US 9,011,333 B2
(45) Date of Patent: Apr. 21, 2015

(54) WIRELESS MOLECULAR SENSOR SYSTEM AND PROCESS

(75) Inventors: Randolph K. Geissler, Minneapolis, MN (US); Scott Nelson, Eagan, MN (US); Steve Lewis, Bloomington, MN (US)

(73) Assignee: VeriTeQ Acquisition Corporation, Delray Beach, FL (US)

( * ) Notice: Subject to any disclaimer, the term of this patent is extended or adjusted under 35 U.S.C. 154(b) by 935 days.

(21) Appl. No.: 13/105,495

(22) Filed: May 11, 2011

(65) Prior Publication Data

US 2011/0282175 A1 Nov. 17, 2011

Related U.S. Application Data

(60) Provisional application No. 61/333,490, filed on May 11, 2010.

(51) Int. Cl.
- *A61B 5/05* (2006.01)
- *A61B 5/145* (2006.01)
- *A61B 5/00* (2006.01)

(52) U.S. Cl.
CPC .......... *A61B 5/14503* (2013.01); *A61B 5/0031* (2013.01)

(58) Field of Classification Search
USPC .......... 600/309, 316, 345–347, 365; 606/167, 606/181–183; 604/64–66; 702/19, 22–23; 204/403.01–403.15; 422/50, 420–429; 436/68; 435/4–5, 14
See application file for complete search history.

(56) References Cited

U.S. PATENT DOCUMENTS

| | | | |
|---|---|---|---|
| 6,699,667 B2* | 3/2004 | Keen | 435/6.11 |
| 7,097,662 B2 | 8/2006 | Evans et al. | |
| 7,340,941 B1 | 3/2008 | Fruhberger et al. | |
| 2003/0004403 A1 | 1/2003 | Drinan et al. | |
| 2005/0136483 A1 | 6/2005 | Carlson | |
| 2005/0221276 A1* | 10/2005 | Rozakis et al. | 435/4 |
| 2007/0027385 A1* | 2/2007 | Brister et al. | 600/365 |
| 2009/0014340 A1 | 1/2009 | Williams et al. | |

FOREIGN PATENT DOCUMENTS

| | | |
|---|---|---|
| WO | WO 2008/067298 A1 | 6/2008 |
| WO | 2010/007580 A1 | 1/2010 |
| WO | WO 2010/007580 A1 | 1/2010 |

OTHER PUBLICATIONS

Yongjun Zhao et al.: "A MEMS viscometric sensor for continuous glucose monitoring", Journal of Micromechanics & Microengineering, Institute of Physics Publishing, Bristol, GB, vol. 17, No. 12, Nov. 14, 2014, pp. 2528-2537, XP020129924, ISSN: 0960-1317.
Extended European Search Report issued on Jul. 21, 2014 in European Patent Application No. 11781213.1.

* cited by examiner

*Primary Examiner* — Michael D'Angelo
(74) *Attorney, Agent, or Firm* — Stroock & Stroock & Lavan LLP

(57) ABSTRACT

Wireless molecular sensor methods and systems integrate radio frequency (RF) technology to interrogate, power, operate and/or readout signals corresponding to levels of molecules of interest from microelectromechanical systems (MEMS) implanted within the body. Various alternative embodiments are disclosed.

13 Claims, 6 Drawing Sheets

WIRELESS MOLECULAR SENSOR SYSTEM AND PROCESS

RELATED APPLICATIONS

This application claims the benefit of, and priority to, U.S. Provisional Patent Application No. 61/333,490, filed May 11, 2010, entitled "Wireless Molecular Sensor," the contents of which are hereby incorporated by reference in their entirety.

FIELD OF THE INVENTION

This disclosure relates generally to methods and systems that integrate radio frequency (RF) technology to interrogate, power, operate and/or readout signals corresponding to levels of molecules of interest from microelectromechanical systems (MEMS) implanted within the body.

BACKGROUND

For medical diagnosis, treatment, and monitoring, it is often necessary to measure relevant molecules from biological tissues and fluids. It has long been desirable to make these chemical measurements without invasive procedures, like withdrawing blood. Implantable devices have been developed using electrochemical sensors embedded beneath the skin to measure the concentration of relevant chemicals in blood or interstitial fluid. For example, implantable devices have been developed to measure blood glucose in a diabetes mellitus patient.

These devices suffer from several deficiencies. One significant problem is a power source necessary to drive the sensing element and process signals obtained therefrom into useful information. An obvious power source for such implantable devices is batteries. Batteries have a number of shortcomings, however. High-capacity batteries exhibiting long life are large and bulky, and therefore not ideal for long-term implantation. Lowering battery capacity will decrease the size of the implanted unit, however useful life of the device will also be shorter. Replacement of an implantable device for any purpose may require surgery, therefore more frequent invasive procedures may be required to change batteries more often. In addition, the electrochemistries responsible for battery function are often based on hazardous and/or toxic substances like mercury or cadmium that pose a risk of injury to the patient. The problem with power sources for such implanted sensing devices is further intensified when the electrochemical sensing platform becomes a closed-cycle system—i.e., is reversible to allow sensing without consumption of any active agent. When a closed-cycle sensing chemistry is included, the need for long-lived implanted power systems is even more acute.

Therefore it is desirable to develop an implantable device that can power a sensor without the use of batteries. In the prior art, U.S. Pat. No. 7,125,382 (Zhou et al.), incorporated herein by reference in its entirety, describes an implantable biosensor system that uses radio frequency identification (RFID) technology, including a remote transponder that is in wireless communication with a passively powered on-chip transponder. The system is specifically adapted to provide a substantially stable and precise voltage to a sensor assembly that is included with an implantable on-chip transponder. The remote transponder is placed within a predetermined distance of the on-chip transponder in order to supply power to and request telemetry data from the on-chip transponder. The remote transponder is also configured to remotely receive data representative of a physiological parameter of the patient as well as identification data and may enable readout of one or more of the physiological parameters that are measured, processed and transmitted by the on-chip transponder upon request by the remote transponder.

However, devices in the prior art are typically based on electrochemical sensors. A physical sensor that functions without the need for batteries is needed.

SUMMARY

The present invention provides methods and systems for reversibly measuring and wirelessly communicating molecular analyte levels using an implantable sensor device operable without the use of batteries.

Embodiments of the present invention advantageously power the sensor using RF energy instead of a battery. RF energy can, in certain cases, interfere with the small signal that a sensor would usually emit. The present invention, however, uses the RF to sense and communicate changes in MEMS devices coated with analyte binding technology.

The implantable biosensor systems disclosed herein use RF technology to wirelessly transmit information between a transponder passively powered on a chip and a remote transponder. Information transmitted via this wireless communication system quantifies a physiological parameter of a patient with respect to the analyte measured by the biosensor. According to one or more embodiments of the invention, the molecular detection method involves the use of a microelectromechanical system (MEMS) device capable of converting physicochemical changes in the environment into an electrical signal that can carry information. In certain preferred embodiments, the MEMS device is coated with certain chemicals that serve to bind to a particular analyte of interest. Such binding can be calibrated to reflect the amount of that analyte registered by the sensor when implanted in a patient. In further embodiments of the invention, various MEMS device designs, surface preparations, and/or surface treatments may be used to improve the sensitivity of measurements obtained. Electrical circuits widely known in the art can be used to generate a voltage signal corresponding to MEMS device response that correlates with the amount of an analyte present.

Additional features and advantages of the present invention are described further below. This summary section is meant merely to illustrate certain features of the invention, and is not meant to limit the scope of the invention in any way. The failure to discuss a specific feature or embodiment of the invention, or the inclusion of one or more features in this summary section, should not be construed to limit the invention as claimed.

BRIEF DESCRIPTION OF THE DRAWINGS

The foregoing summary, as well as the following detailed description of the preferred embodiments of the application, will be better understood when read in conjunction with the appended drawings. For the purposes of illustrating the device of the present application, there is shown in the drawings preferred embodiments. It should be understood, however, that the application is not limited to the precise arrangements and instrumentalities shown. In the drawings:

FIG. 4 illustrates two exemplary MEMS devices.

DETAILED DESCRIPTION

The present invention provides a wireless molecular sensor encompassing, in various embodiments, analyte binding with surface chemical affinity coatings, and mass detection with a MEMS device powered by an excitation RF signal from an external reader. In some embodiments, the invention also provides methods and systems for frequency analysis of signals from a MEMS device. The wireless molecular sensor described herein is implantable, and can detect and communicate levels of analytes in an animal, including humans.

As used herein, the term "analyte" refers generically to any molecule of interest that is capable of being detected by another molecule that may be coated on the surface of a MEMS device. For the purposes of this invention, an analyte is not inherently limited to any particular chemical structure or composition. Non-limiting examples of analytes relevant for medical diagnostic and monitoring purposes are peptides, proteins, sugars, nucleic acids, and further include pathogens such as bacteria, fungi and viruses.

As used herein, the term "coating agent" refers generically to a molecule capable of coating the surface of a MEMS device and further capable of recognizing an analyte with some degree of specificity. Non-limiting examples of coating agents include naturally-occurring and artificial receptors, lectins, antibodies, antigen-binding particles, chemical compounds and nucleic acids.

As used herein, the term "sensor" refers to the implantable device. The sensor contains the MEMS device with a preferred surface finish and applied receptor technology. It also contains electronics necessary for self activation when present in a prescribed electromagnetic field and means to transmit signal data to an external reader.

The external "reader" is the device used to read the implanted sensor. It contains a power amplifier to radiate and activate the sensor. It also contains a power source, means to gather data from the sensor, and means to report the data to a user.

As used herein, the term "MEMS" or microelectromechanical systems refers to the integration of mechanical elements, sensors, actuators, and electronics on a common silicon substrate through nanofabrication technology.

Figure 1:
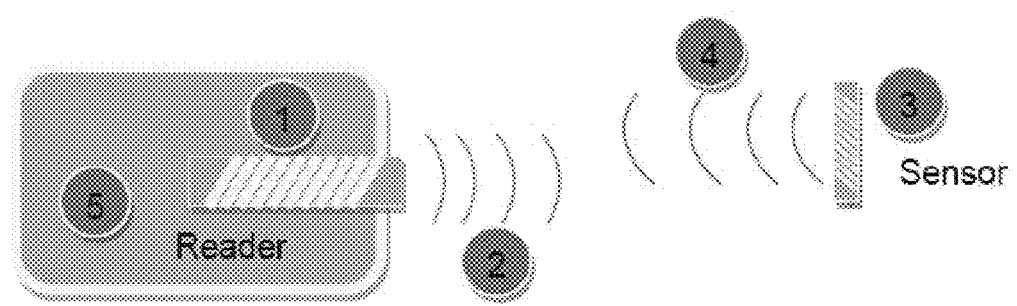
FIG. 1 is a diagram illustrating a wireless molecular sensor system and process according to some embodiments of the invention.

An exemplary process of using a wireless molecular sensor of the present invention is illustrated in FIG. 1. At 1, the user initiates a request for data. At 2, the reader transmits electromagnetic energy to the sensor. At 3, the electromagnetic field is converted to an electrical charge, which is used for powering the sensor. At 4, the sensor responds to the reader by encoding the analyte binding data and modulating the electromagnetic field. At 5, the reader receives the transponder's data, decodes the data, and reports the data to the user.

The in vivo sensor of the present invention is, in some embodiments, passive. It does not have its own power source, such as a battery. The sensor is electrically inactive until activated by an external reader. (The sensor chemistry, however, may always be active.) In preferred embodiments, the reader radiates an electromagnetic field specifically tuned for the sensor. The sensor harvests power from the reader's electromagnetic field and then modulates the field, sending analyte binding data back to the reader.

Figure 2:
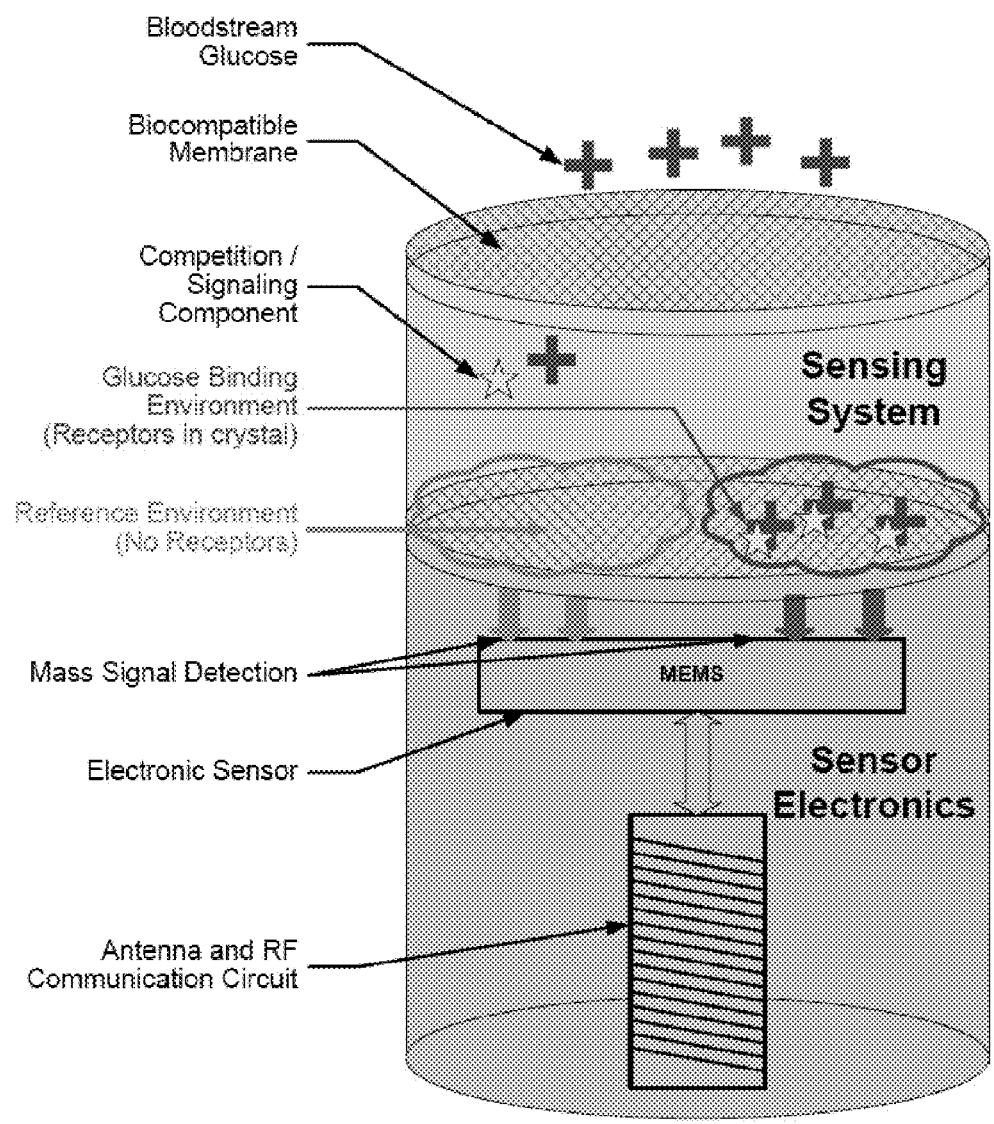
FIG. 2 is an schematic diagram of a molecular sensor according to some embodiments of the invention.

A schematic of a molecular sensor according to some embodiments of the invention is shown in FIG. 2. FIG. 2 depicts an in vivo bio-stable molecular sensor that can reversibly measure and wirelessly communicate molecular analyte levels (e.g., glucose in the blood). In one or more embodiments, the sensor comprises a self-contained sensing system, interfaced with a compatible signal transduction unit, contained in bio-stable device with a biocompatible interface. The sensing system includes at least one osmotic membrane, through which the analyte can flow bi-directionally, but which any competitive binding molecule optionally used in the sensing system cannot pass through.

As shown in FIG. 2, in certain preferred embodiments, glucose levels may be measured using a MEMS device coated with glucose binding receptors. A biocompatible membrane allows bloodstream glucose to pass through and be sensed, but does not allow a larger molecular weight molecule that competes with glucose for binding the receptors to exit the solution space of the sensor. A reference environment, with no coating agent, or a different coating agent, may optionally be included in the MEMS and is also shown.

The MEMS, sensor electronics, and packaging are preferably integrated into a sensor of small size suitable for implantation in an animal. Dimensions may vary, but in some embodiments are less than two inches, preferably less than one inch, most preferably about 50-150 mm.

Figure 3A:
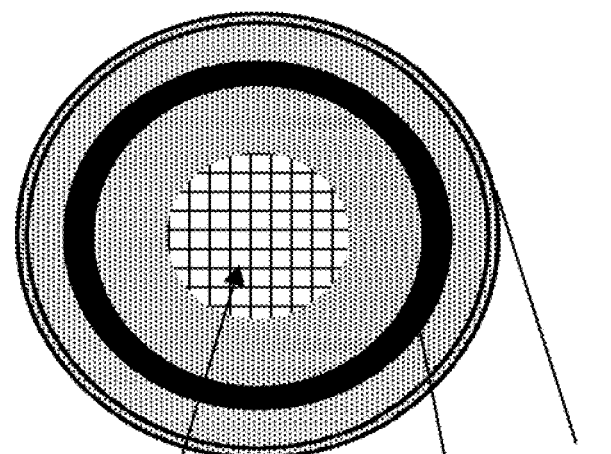
FIG. 3 is a schematic diagram showing exemplary sensor elements in an exemplary bio-stable packaging, from a top surface view (FIG. 3A) and a cross sectional view (FIG. 3B).
Figure 3B:
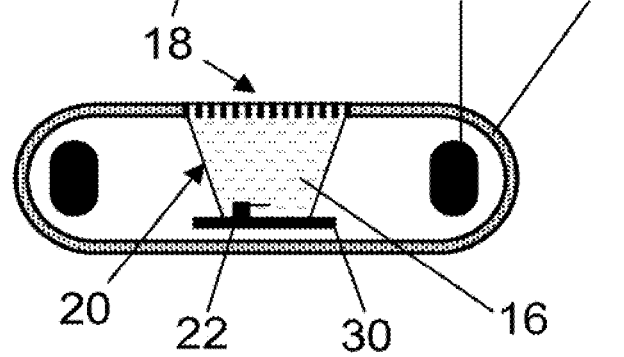

FIG. 3 is a schematic showing exemplary elements of a molecular sensor according to various embodiments of the invention in an exemplary implantable housing. FIG. 3A is a top sectional view, and FIG. 3B is a horizontal cross-sectional view. The implantable housing includes an outer housing generally identified as 12, which houses an annular wire coil 14. A solution well, cavity, or other space, generally identified as 16, is bounded by one or more solid side support walls 20, a semi-permeable membrane 18, and an integrated circuit (IC) chip also functioning as a solid support 30. As described below, the semi-permeable membrane 18, permits fluid to enter the solution well through the membrane. As illustrated in FIG. 3B, in some embodiments, the IC chip and solid support 30 provide a base upon which one or more MEMS devices, generally illustrated as 22, may be mounted.

The housing 12 or packaging for the system can be fashioned from one or more of a variety of biocompatible materials suitable for long-term implantation in a human or other animal. Such materials include glass, plastics, synthetic carbon- or silicon-based materials, fluoropolymers like PTFE, PFA or ETFE, or non-reactive metals useful in the art as implantable medical replacements, prostheses and devices. The housing should be designed to be substantially fluid and gas impermeable, with the possible exception of one or more portions bounding the solution 16, i.e., membrane 18 described below, that will remain in direct contact with the aqueous environment to permit measurement of particular analytes therein.

The molecular detection portion of the apparatus resides in a well/space 16 that is in fluidic contact with fluids in the extracellular space of the patient after implantation of the device. In addition, the solution well 16 must be isolated from the remainder of the housing which is designed to accommodate electronics on the integrated circuit and the RF antenna. The isolation of the solution well 16 from the remainder of the housing may be accomplished by any one of a number of means including one or more support walls 20. FIG. 3B shows a conical shaped well; however, other shapes and configurations may be used to enclose solution well 16. In other embodiments, for example, the solution cavity of the sensing system may be cylindrical, rectangular, etc. A fluid tight seal may be created between the support walls 20 and IC chip/base 30 using any of a number of well known materials such as epoxies and/or chemical sealants for bonding the support walls to the IC chip/base.

In some embodiments, the invention includes a semi-permeable membrane 18 physically isolating the sensing system from the implanted environment while permitting analytes of interest to enter the sensing system through normal diffusion. Thus, the system can, in some embodiments, substantially exclude non-relevant chemicals and biological agents in bodily fluids that may interfere with the fidelity of signals produced by the sensor. Similarly, the system can, in some embodiments, substantially include (block the outward diffusion of) certain molecules that may be used as part of the sensing system (e.g., competitive binding molecules) based, for example, on a difference in molecular weight relative to the analyte of interest. Different types of selectively permeable membranes known in the art can be used in the present invention, including membranes that exclude particles based on size, charge, hydrophobicity or hydrophilicity, or, in some cases, that are selectively permeable for a given molecule. Semi-permeable membrane 18 is biocompatible, and is preferably able to persist in vivo after implantation for long periods of time. Biocompatible membranes are preferably also non-biofouling, meaning that they resist the undesirable accumulation of biological materials, such as cells and cell fragments, and microorganisms like bacteria, algae, or fungi.

In addition to membrane 18, the solution well 16 is also formed by the solid support 30 comprising the IC chip securably mounted to a wall or suitable structural element such that the surface of the support base is exposed to solutions in the solution space 16. In one embodiment, the support base is mounted to the reverse side of the integrated circuit. One or more MEMS devices 22 are disposed upon the surface of the support base 30 facing solution well 16 for detecting one or more analytes therein.

Figure 4A:
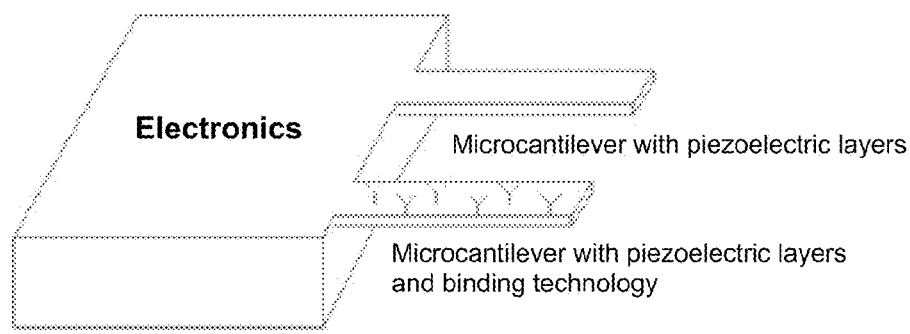
FIG. 4A shows a dual beam microcantilever and FIG. 4B shows a resonant disc.

In some embodiments of the invention, MEMS device 22 is a microcantilever, as shown schematically in FIG. 4A. Biosensors for clinical applications based on microcantilevers have been described in the prior art (see, e.g., Hwang, K. S., et al., Ann Rev. Anal. Chem. 2:77-98, 2009, incorporated herein by reference). Microcantilevers are microelectromechanical systems (MEMS) that can be micromachined and mass-produced, for example, from single crystal silicon wafers, but may be fashioned from other materials. Microcantilevers offer high sensitivity and selectivity for a wide variety of biological and chemical sensing. Changes in the physical properties of a microcantilever (or other MEMS device) are used to detect changes in the environment of the microcantilever. These include, but are not limited to, mass changes, as the response of piezoelectric MEMS devices may also reflect other variables.

In some embodiments, the microcantilevers may be coated with one or more agents. Deflection or conductivity of the microcantilever can reflect the presence or absence of a certain analyte depending on binding interactions with an agent (the "coating agent") adherent to one or more beams of the cantilever. As used in the present invention, microcantilever operation refers generically to coating agent-analyte interactions, although it should be understood that other more specific interactions are subsumed within this general definition, e.g., receptor-ligand, antibody-antigen, lectin-carbohydrate, etc.

Microcantilevers can detect analytes in various ways. A first mode of microcantilever operation is sometimes referred to as either the "static" or "deflection" mode. The static mode measures analyte molecule binding to the coating agent on the surface of the cantilever through an increase in mass on the coated side of the cantilever beam. This mass increase creates tension on the cantilever, causing a physical deflection of the cantilever. The amount of deflection is usually in nanometer lengths that may be measured using various techniques known in the art such as optical techniques and piezoelectric methods. In the static mode of operation, the concentration of the analyte can be determined by the degree of deflection. As an alternative, the coating agent may exist at equilibrium already "bound" to a third molecule and, when present, an analyte can "compete" with the third molecule for binding to the coating agent. In some embodiments, the third molecule may be heavier than the analyte, so analyte molecule binding to the coating agent on the surface of the cantilever may result in a decrease in mass. This "competitive binding" mode of operation can be useful, for example, as a screening method for identifying or discovering new analytes that may bind to a known receptor. Such screening methods are well known in the art.

Another mode of microcantilever operation is referred to as either the "dynamic" or "resonance" mode. In the dynamic mode, energy is supplied to the cantilever beam to oscillate at a particular resonant frequency. As with the static mode, analyte binding to coating agent on one side of the beam will change its mass; an increase or decrease in mass will change the resonant frequency for the same amount of energy applied to the cantilever beam. The detection of a change in the cantilever's natural resonant frequency may include, for example, detecting an amplitude change while resonating at the original frequency and/or sweeping the frequency to find the new resonant frequency. A variety of techniques, including thermal, electrostatic, and magnetic excitation methods, have been developed for actuating resonance in a microcantilever, and are known in the art.

Direct microcantilever-based monitoring of biomolecular binding events in situ or in vivo, or in aqueous environments generally, most often utilizes the static mode of operation. Dynamic (resonance) microcantilever detection is typically performed in air or in vacuum because the quality factor, or Q factor, decreases substantially in an aqueous environment, degrading the resolution of the sensors. (The quality factor describes resonant object's bandwidth relative to its center frequency. A higher quality factor indicates a lower rate of energy loss relative to the stored energy of the oscillator, causing the oscillations to die out more slowly.) Therefore physical barriers exist that tend to limit the routine operation of microcantilevers in dynamic (resonance) mode in an aqueous environment like the interior of a human or animal. Despite these limitations, however, dynamic detection of biologically relevant compounds in aqueous environments has been described. For example, Lee et al. (Lab Chip 4:547-52, 2004) describes in situ antibody-based detection of a prostate-specific antigen using resonant frequency shift detection in a piezoelectric material layer-embedded microcantilever. In one or more preferred embodiments, the invention utilizes one or more microcantilevers operating in dynamic (resonance) mode.

Figure 4B:
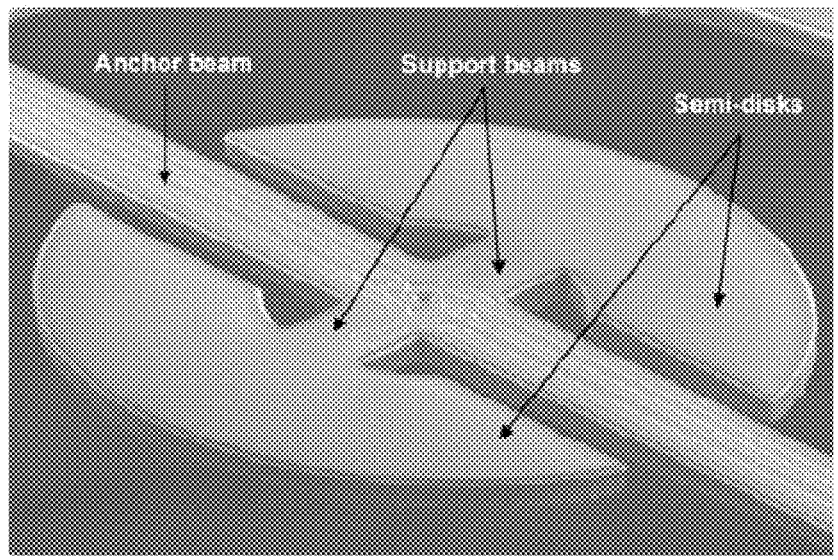

In alternative embodiments, various other MEMS device designs may be utilized to maximize mass sensitivity in a low Q environment. In some embodiments of the invention, for example, the MEMS device may be a resonant disc, as illustrated schematically in FIG. 4B (see, e.g., Seo, J. H. and Brand, O., J. Microelectromechanical Systems 17(2):483-493, 2008, incorporated herein by reference). The MEMS device may also be a high order mode cantilever (see, e.g., Ghatkesar, M. K. et al., App. Phys. Lett. 92: 043106, 2008, incorporated herein by reference) measuring higher order effects. These MEMS devices are exemplary; other MEMS designs may be used.

In some embodiments, fabrication of the MEMS devices comprises deposition and patterning of up to seven layers of material. Each deposition and patterning step may be followed by characterization to determine the success of the processing step.

In some embodiments, one or more cleaning and/or preparation processes may be performed prior to coating the MEMS device, so that the MEMS is not damaged by an incompatible chemical or process.

In addition, or in the alternative, one or more surface treatments may be applied to the MEMS devices prior to coating, for increased signal response. Such surface treatments may include, for example, any compatible surface treatment that increases the surface area of the MEMS device for coating with a coating agent (e.g., with analyte receptors), thereby increasing the ability of the MEMS device to capture analyte molecules and increasing device sensitivity. Exemplary surface treatments include those producing porous or patterned surfaces (see, e.g., Stolyarova, S. et al., Sensors and Actuators B 131:509-515, 2008 and Lee, D. et al. Sensors and Actuators B 137:561-565, 2009, each incorporated herein by reference). Variations on these types of surfaces, different types of surfaces, and/or mixtures of surfaces may be used.

MEMS devices can utilize a variety of known surface chemistries for analyte capture. Multiple chemistries for the capture of various analyte molecules on a surface have been recorded in the literature. For example, surfaces may be coated with agents having a high affinity for an analyte, such as antibodies, enzymes, and natural receptors.

Artificial chemical receptors have also been described, and can likewise be adapted for surface detection of analytes by MEMS devices. For example, boronic acid-based chemicals have been shown to effectively function as sugar-specific receptors. The covalent pair-wise interaction between certain boronic acids and the 1,2- or 1,3-diols characteristic of simple sugars like glucose and fructose in aqueous systems is rapid and reversible. As such, the equilibrium established between boronic acids and the hydroxyl groups present on saccharides can provide a range of sensors for saccharides. One advantage of this dynamic covalent strategy is the ability of boronic acids to overcome the challenge of binding neutral species in aqueous media.

Other artificial receptor systems may be employed in further embodiments within the scope of the present invention. For example, U.S. Pat. No. 7,469,076 (Carlson), incorporated herein by reference, discloses combinatorial arrays of artificial receptors operating as a sensor system for the detection of particular analytes in a solution. This approach, called CARA™, is based on the idea of using a small library of subunits to access both the breadth and depth of "binding space" for a given analyte. In nature, this strategy is mirrored by antibody-antigen binding, which relies on a small repertoire of the 20 common amino acids to achieve a virtually infinite diversity of binding interactions with an antigen. The key to this success is the combinatorial display of these 20 amino acid "building blocks" within a defined binding pocket. An array of receptor environments is created through the simple solution combination of these building blocks, which can then be covalently immobilized to a support surface on a MEMS device.

Artificial receptors may also be used on MEMS devices in combination with macromolecules such as, but not limited to, dextrans or dendrimers (see, e.g., Fréchet, J. M. J., Proc. Natl. Acad. Sci. 99:4782-87, 1999, incorporated herein by reference). Dendrimers in particular have received great attention in recent years due to their capacity for specific molecular recognition. Various embodiments of the present invention incorporate their use, for example, as ligands that compete with the target analyte for binding at the artificial receptor. A macromolecule bound to the surface receptor may be displaced by an analyte having a much lower mass, decreasing the tension on the microcantilever beams. Significant changes in mass can thus be detected by a MEMS device (e.g., a microcantilever device operating in either deflection or resonance mode) and provide a means of measuring the relative concentration of the target analyte in a sample or in vivo. In this way, MEMS devices can be used to follow binding and unbinding events of analytes to surface-bound receptors.

According to some embodiments, for microcantilever operation in the static mode, at least two microcantilevers are used. As shown in FIG. 4A, a first microcantilever beam is coated with a coating agent, and is capable of detecting the presence of analytes in the aqueous environment through the methods described above. A second non-coated microcantilever is present to serve as a reference for a differential measurement, that can in addition help minimize common mode noise. In alternative embodiments, at least two microcantilevers may be used, for example, with different coatings or different coating levels on each microcantilever, for further characterization/analysis of analyte binding and/or detection of multiple analytes binding.

Microcantilevers and microcantilever arrays operating in the dynamic or resonant mode may not require a control or reference microcantilever as described above. They may, nonetheless, have one or more additional microcantilevers (e.g., a second coated microcantilever).

Microcantilever arrays containing a plurality of microcantilevers (whether coated or non-coated) can be provided to increase binding capacity and/or improve the signal sensitivity of target analyte binding. Such arrays have been described in the art (e.g., as developed for "lab-on-a-chip" applications) and their use is specifically within the scope of the present invention.

Figure 5:
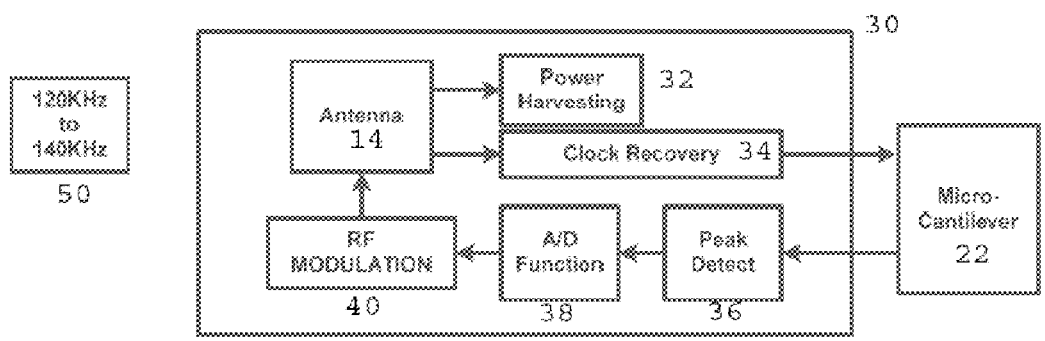
FIG. 5 is a sensor electronics block diagram, illustrating basic circuit components according to some embodiments of the invention.

FIG. 5 shows a block diagram of exemplary circuit components of a wireless molecular sensor 30 according to some embodiments of the invention. It is understood that the term "circuit," although used in the singular form, can refer to multiple individual circuits or groups of circuits. As is described in greater detail below, the annular wire coil 14 serves as an antenna for reading RF signals over a range of frequencies, preferably a low frequency (in a KHz range, e.g., between 120 and 140 KHz), from an external reader 50. This signal is coupled to a power recovery circuit 32 to provide a DC voltage to power the clock recovery circuit 34 and other elements on the IC chip 30. The clock recovery circuit 34 receives the signal from the antenna 14 and applies a clock signal that is either at the frequency or at a harmonic of the frequency of the RF input signal. The clock signal is applied to the one or more microcantilever device(s) 22 (a microcantilever is described in this example; however a resonant disc or other MEMS device may be used) for energizing the microcantilever beam in either a static or a resonance mode, as described in detail below. A signal detection circuit 36 detects the changes in the microcantilever device(s) resulting from interactions between analytes and coating agents in the solution well. More than one signal detection circuit may be employed to obtain relevant information from the microcantilever. In addition, other circuits, such as signal conditioning circuits, may be present. The signal is passed to an analog-to-digital converter 38, which converts the signal to a digital representation of the changes in load and/or resonance of the microcantilever device(s). This digital signal is used to alter the RF transmission signal sent through the antenna by a specific RF modulation circuit 40; changes in this output are recorded by the external reader 50, and, as described below, reflect changes in signal levels (resonant frequency, load, etc.) reported by the microcantilever device(s) that correlate with the binding of specific analytes to coating agents on the microcantilever beams.

Each microcantilever 22 described above is under the control of an integrated circuit that incorporates several components or blocks, described individually below. These electronics reside in the fluid- and gas-impermeable portion of the housing 12, described above. The electronic circuitry described in connection with the present invention provides a method for detecting mass reported from the microcantilever devices operating in both static and dynamic modes. The disclosure of the components or blocks described herein is presented to support the present invention and is not intended to limit the invention to these components. It is therefore understood that more components may be added or subtracted or substituted with equivalent blocks or circuits performing substantially the same function.

The use of antennas in radio frequency (RF) systems, particularly RF identification systems, has been in widespread use. For example, an antenna element is a feature of Passive Integrated Transponder (PIT) tags that permits these devices to be embedded in or attached to a wide variety of items to be tracked and accounted for (see, e.g., U.S. Pat. Nos. 5,211,129; 5,223,851; and 5,281,855 each of which is incorporated herein by reference). In the present invention, and consistent with their use in the prior art, the antenna 14 of the present invention may be a coil of wire or a coiled wire wrapped around a ferrite rod. The antenna has both receiving and transmitting signals according to instructions provided by the integrated circuit. In addition, coils receiving radio signals generate electromagnetic energy that can be converted to a direct current to power the integrated circuit and generate the transmitting signal. Preferably, the reading and sensing antenna 14 of the present invention is tuned so that the resonant frequency of the antenna matches the transmit frequency. In one or more embodiments, antenna 14 is a wire wound helical antenna. However, other sensor antenna designs with differing geometries, efficiencies, impedance, bandwidth, and gain may be used.

IC chip 30 provides power harvesting at 32 to rectify and filter the RF signal and generate sufficient DC power from the electromagnetic waves received by antenna 14 for the passive device to operate. In some embodiments, a single diode or diode bridge is used to rectify the signal, and a capacitor is used to store charge and filter the signal. Power harvesting block 32 provides a DC power source for energizing the rest of the circuit.

The sensor circuit preferably has a clock source for synchronization. In some embodiments, clock recovery 34 is simply a switch or a comparator that has input from antenna 14 and is capable of recovering frequency signals from the sinusoidal waveform captured by the coil. The binary output of the clock tracks the RF input from the antenna with a logic '0' when voltage is below a certain threshold and '1' when voltage is above the threshold. Other data encryption techniques may also be used (e.g., frequency-shift keying). The resulting output is a clock signal having the same frequency as the incoming RF signal.

The microcantilever devices 22 are as described above. In one or more embodiments of the present invention, microcantilever 22 is a MEMS structure with several layers. One layer is a piezoelectric layer that deflects the beam when voltage is applied. The frequency of the voltage signal driving the microcantilever beam is obtained from the clock recovery circuit 34. A piezoresistive layer can be incorporated to measure the deflection of the beam. As described above, a mass change on the cantilever beam will effect a change of the response of the cantilever to the resonating stimulus provided by the piezoelectric layer. Although the term "microcantilever" is used in various examples to describe the present invention, this term is not intended to limit this disclosure to cantilever devices of any particular dimension or size, nor is it intended to limit this disclosure to MEMS devices comprising cantilevers, as other MEMS designs with similar operating principles may be used in wireless molecular sensors of the present invention.

A signal detection circuit 36 may be implemented to condition the voltage signal from the microcantilever. Several different conditioning methods may be used in various embodiments to transfer the digital data to the external reader 50. In addition, valuable information may be obtained by tracking the rate of change over time in the signal. In one embodiment, the signal detection circuit may function as a simple peak detection circuit that tracks supra-threshold voltage signals generated by the microcantilever sensor. The peak signal from the sensor correlates to the amount of analyte on the MEMS cantilever. A transistor may be included in this circuit so that the peak detector can be reset by draining the capacitor by temporarily providing a path to ground. The peak detection preferably consists of a circuit such as a diode that will minimize the discharge and a capacitor that retains the highest voltage found since the last peak reset. The voltage will increase when the input increases, but will hold charge when voltage drops below that level.

A simple analog to digital (A/D) converter 38 may also be implemented, which translates the analog voltage from the peak detection circuit 36 into digital number. The digital output is then used as the input to the RF modulation block 40.

At RF modulation block 40 the RF signal is modulated. Various modulation techniques may be used to modulate the RF signal, including, but not limited to, amplitude modulation (AM), frequency-shift keying (FSK), phase-shift keying (PSK), etc. The modulation may be performed, for example, by using a transistor to force one side of the antenna to ground at a specific rate (the data rate). The modulation is decoded by the reader/external receiver 50. The modulation can be as simple as a transistor that has the drain connected to the antenna, source connected to the ground, and the gate connected to the output of the RF modulation scheme. This way the transistor will turn on and off depending on the A/D value, which correlates with the peak signal from the sensor, which further correlates with the amount of analyte detected by the microcantilever. In alternative embodiments, other methods can be used to transfer the digital data to the reader. In addition, other techniques for modulation, including analog and digital modulation, may be used.

External reader 50 transmits an RF signal at a given frequency that is related to the drive frequency of the microcantilever beam. In a preferred embodiment, presented herein for exemplary purposes only and not intended to limit the scope of frequencies useful for this function, the transmit frequency is a low frequency in the KHz range (e.g., between 120 KHz and 140 KHz). Other frequencies, higher or lower than this range may be used in alternative embodiments. External reader 50 will also detect the return signal from the antenna on the sensor. The RF modulation of the signal by the sensor at the defined data rate is decoded, and the amount of analyte present, as detected by the microcantilever, is determined from this digital data stream.

Figure 6:
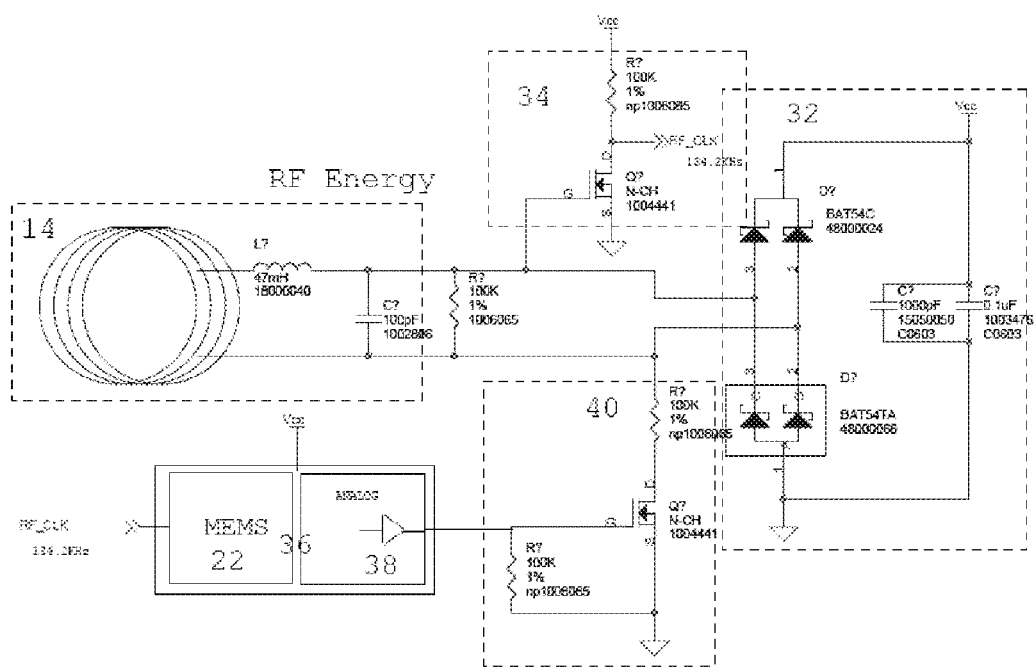
FIG. 6 is an exemplary schematic of sensor device electronics.

FIG. 6 is an exemplary schematic of sensor device electronics. Portions of this schematic corresponding to elements in the block diagram in FIG. 5 are labeled with corresponding numerals (and, for the antenna 14, power harvesting 32, clock 34, and RF modulation 40 portions, boxes with dotted lines).

In some embodiments, the external reader can, for example, perform a frequency analysis of the microcantilever to derive the mass of the analyte present on the microcantilever beam. Such a frequency analyzing system may have design and electronics as described above for a simple resonant device; however, the frequency analyzed system may, in some embodiments, not require a reference microcantilever. Calibration of signals obtained from the microcantilever can be achieved using a number of methods known in the art of ligand-receptor binding. As in a simple resonant mode, in the frequency analyzing mode the external reader will provide the excitation and demodulate the return signal. However, for frequency analysis, the external reader will vary the frequency and monitor the peak value obtained at each frequency. (In some embodiments, the peak value may be a root mean square value over a small frequency range, or another value representative of the peak value.) After the reader sweeps through the entire frequency range, the quality factor (Q-value) and the resonant frequency of the microcantilever can be calculated. These values will be proportional to several different variables, including the frequency response of the coil, the dimensions of the microcantilever, the pressure and/or viscosity of the surrounding fluid and the changes to the weight of the microcantilever beam—a value that can be correlated with the relative number of analyte molecules present. The frequency is preferably swept at a rate such that the effects of the fluid pressure are the same for all frequencies. The device can be calibrated to account for all variables other than weight (e.g., fixed physical parameters such as the antenna and the mechanical structure), therefore the change in Q value and/or resonant frequency can be correlated to changes in mass and, in turn, analyte concentration. The external reader preferably stores a recent history of values thus obtained so that the user may determine whether analyte values are rising or falling.

While there have been shown and described fundamental novel features of the invention as applied to the preferred and exemplary embodiments thereof, it will be understood that omissions and substitutions and changes in the form and details of the disclosed invention may be made by those skilled in the art without departing from the spirit of the invention. Moreover, as is readily apparent, numerous modifications and changes may readily occur to those skilled in the art. Hence, it is not desired to limit the invention to the exact construction and operation shown and described and, accordingly, all suitable modification equivalents may be resorted to falling within the scope of the invention as claimed. It is the intention, therefore, to be limited only as indicated by the scope of the claims appended hereto.

What is claimed is:

1. A system for wireless detection of an analyte in vivo, comprising an implantable sensor and an external reader,
    said sensor comprising at least one microelectromechanical system (MEMS) device sensing the analyte, said MEMS device coupled to an integrated circuit for communicating with the reader,
    said reader transmitting radio frequency (RF) energy powering the sensor and receiving RF signals from the sensor related to changes in the MEMS device reflecting levels of analyte,
    wherein the MEMS device is a microcantilever, and
    wherein the system determines analyte levels by measuring changes in amplitude of oscillation of the MEMS device.

2. The system of claim 1, wherein the MEMS device is a dual beam microcantilever.

3. The system of claim 1, wherein the MEMS device is coated on one or more surfaces with at least one coating agent.

4. The system of claim 3, wherein one or more smooth surfaces of the MEMS device are treated to increase surface area for the coating agent.

5. The system of claim 3, wherein the coating agent is a boronic acid-based chemical.

6. The system of claim 3, wherein the coating agent is an artificial receptor.

7. The system of claim 6, wherein the artificial receptor is used in combination with a competitive binding molecule.

8. The system of claim 7, wherein the competitive binding molecule is at least one of a dextran and a dendrimer.

9. The system of claim 1, wherein the sensor further comprises a semi-permeable membrane positioned between the MEMS device and bodily fluids.

10. The system of claim 1, wherein the system determines analyte levels by measuring changes in amplitude of oscillation of the MEMS device.

11. The system of claim 1, wherein the reader transmits and receives RF energy in the KHz range.

12. The system of claim 1, wherein the analyte is glucose.

13. The system of claim 1, wherein said integrated circuit further comprises one or more of: an antenna, a power harvesting component, a clock component, a signal detection component, an analog to digital converter component, and an RF modulation component.

* * * * *